United States Patent
Porter et al.

(10) Patent No.: US 8,828,733 B2
(45) Date of Patent: Sep. 9, 2014

(54) MICROSENSOR MATERIAL AND METHODS FOR ANALYTE DETECTION

(75) Inventors: Timothy L. Porter, Flagstaff, AZ (US); Ray Stewart, Belmont, CA (US); Timothy L. Vail, Parks, AZ (US)

(73) Assignees: Cantimer, Inc., Menlo Park, CA (US); Arizona Board Of Regents For And On Behalf Of Northern Arizona University, Scottsdale, AZ (US)

( * ) Notice: Subject to any disclaimer, the term of this patent is extended or adjusted under 35 U.S.C. 154(b) by 909 days.

(21) Appl. No.: 12/523,708

(22) PCT Filed: Jan. 18, 2008

(86) PCT No.: PCT/US2008/000672
§ 371 (c)(1),
(2), (4) Date: Feb. 19, 2010

(87) PCT Pub. No.: WO2008/088867
PCT Pub. Date: Jul. 24, 2008

(65) Prior Publication Data
US 2010/0203648 A1    Aug. 12, 2010

Related U.S. Application Data

(60) Provisional application No. 60/881,754, filed on Jan. 19, 2007, provisional application No. 60/926,474, filed on Apr. 27, 2007.

(51) Int. Cl.
*G01N 27/12* (2006.01)
*G01N 5/02* (2006.01)
*G01N 33/00* (2006.01)
*G01N 29/036* (2006.01)

(52) U.S. Cl.
CPC ...... *G01N 29/036* (2013.01); *G01N 2291/0257* (2013.01)

USPC ........... 436/109; 436/100; 436/101; 436/103; 436/106; 436/133; 436/134; 436/148

(58) Field of Classification Search
USPC .......... 436/100–101, 103, 106, 109.133–134, 436/148
See application file for complete search history.

(56) References Cited

U.S. PATENT DOCUMENTS

| 5,571,401 A | 11/1996 | Lewis et al. |
| 5,728,590 A | 3/1998 | Powelll |

(Continued)

FOREIGN PATENT DOCUMENTS

| WO | WO 97/39041 A1 | 10/1997 |
| WO | WO 99/08105 A1 | 2/1999 |

(Continued)

OTHER PUBLICATIONS

Lee, Y.-K. et al, Journal of Polymer Science A: Polymer Chemistry 1999, 37, 3871-3875.*

(Continued)

*Primary Examiner* — Arlen Soderquist
(74) *Attorney, Agent, or Firm* — Jacqueline F. Mahoney; Judy M. Mohr; McDermott Will & Emery LLP

(57) ABSTRACT

The compositions and methods relate to an organic polymer-inorganic particle sensor material for detecting analytes. Interactions between the polymer and the particles are affected by the presence of analyte, which displaces the polymer and increases its free volume. This change in free volume can be detected, e.g., using an embedded piezoresistive microcantilever (EPM) sensor. Analytes that can be detected include noxious substances, such as hydrogen cyanide gas and carbon monoxide.

13 Claims, 2 Drawing Sheets

(56) References Cited

U.S. PATENT DOCUMENTS

| | | | |
|---|---|---|---|
| 5,922,537 | A | 7/1999 | Ewart et al. |
| 5,981,695 | A * | 11/1999 | Mattes et al. ............... 528/492 |
| 6,265,615 | B1 * | 7/2001 | Kaner et al. ............... 564/424 |
| 6,429,282 | B1 * | 8/2002 | Wang et al. ............... 528/422 |
| 6,523,392 | B2 | 2/2003 | Porter et al. |
| 6,664,051 | B1 | 12/2003 | Shinoki et al. |
| 6,773,926 | B1 | 8/2004 | Freund et al. |
| 6,823,717 | B2 | 11/2004 | Porter et al. |
| 6,854,317 | B2 | 2/2005 | Porter et al. |
| 7,168,294 | B2 | 1/2007 | Porter et al. |
| 7,395,693 | B2 | 7/2008 | Porter et al. |
| 2002/0141901 | A1 * | 10/2002 | Lewis et al. ............... 422/82.01 |
| 2003/0010097 | A1 | 1/2003 | Porter et al. |
| 2003/0156953 | A1 * | 8/2003 | Chinn et al. ............... 417/322 |
| 2004/0042933 | A1 * | 3/2004 | Lewis et al. ............... 422/98 |
| 2004/0194534 | A1 | 10/2004 | Porter et al. |
| 2004/0211243 | A1 | 10/2004 | Porter et al. |
| 2005/0164299 | A1 | 7/2005 | Stewart |
| 2006/0053871 | A1 | 3/2006 | Porter et al. |
| 2006/0293510 | A1 | 12/2006 | Shionoya et al. |
| 2007/0119236 | A1 | 5/2007 | Porter et al. |
| 2009/0090168 | A1 | 4/2009 | Porter et al. |
| 2010/0059375 | A1 * | 3/2010 | Weiller et al. ............... 204/433 |

FOREIGN PATENT DOCUMENTS

| | | | |
|---|---|---|---|
| WO | WO 00/00808 | A2 | 1/2000 |
| WO | 00/20852 | * | 4/2000 |
| WO | WO 00/33062 | A1 | 6/2000 |
| WO | 00/78204 | * | 12/2000 |

OTHER PUBLICATIONS

Pei, Q. et al, Journal of Physical Chemistry 1992, 96, 10507-10514.*
Otero, T. F. et al, Synthetic Metals 1996, 83, 205-208.*
Shimoda, S. et al, Electrochimica Acta 1998, 44, 219-238.*
Kiattibutr, P. et al, Reactive & Functional Polymers 2002, 53, 29-37.*
Varela, H. et al, Polymer 2003, 44, 5369-5379.*
Onoda, M. et al, Current Applied Physics 2005, 5, 194-201.*
Houdayer, A. et al, Synthetic Metals 2005, 151, 165-174.*
Zic, M., Journal of Electroanalytical Chemistry 2007, 610, 57-66.*
Frechert, J., "Dendrimers and supramolecular chemistry", *Proc. Natl. Acad. Sci. USA*, 99(8):4782-4787 (2002).
Gunter, R.L. et al., "Invetsigation of DNA sensing using piezoresistive microcantilever probes", *IEEE Sensors Journal*, 4(4):430-433 (2004).
Gunter, R.L. et al., "Viral Detection using an embedded piezoresistive microcantilever sensor", *Sensors and Actuators*, 107(3):219-224 (2003).
Gunter, R.L. et al., "Hydration level monitoring using embedded piezoresistive microcantilever sensors", Medical Engineering & Physics, 27:215-220 (2005).
Hartig, G. et al., "Intramolecular disulphide bond arrangements in nonhomologous proteins", *Protein Science*, 14:474-482 (2005).
Kooser, A. et al., "Investigation of the antigen antibody reaction between anti-bovine serum albumin and bovine serum albumin using piezoresistive microcantilever sensors", *Biosensors and Bioelectronics*, 19:503-508 (2003).
Kooser, A. et al., "Gas sensing using embedded piezoresistive microcantilever sensors", *Sensors and Actuators*, 99(2-3):474-479 (2007).
Lenffer, et al. "CysView: protein classification based on cysteine pairing patterns", *Nucleic Acids Research*, 32:W35-355 (2004).
Porter, T.L. et al., "An embedded polymer piezoresistive microcantilever sensor", *Ultramicroscopy*, 97:365-369 (2003).
Porter, T.L. et al., "A solid-state sensor platform for the detection of hydrogen cyanide gas", *Sensors and Actuators*, 123:313-317 (2007).
Porter, T.L. et al., "Embedded piezoresistive microcantilever sensors: Materials fro sensing hydrogen cyanide gas", *Mater. Res. Soc. Symp. Proc.*, 915:149-153 (2006).
Porter, T.L. et al., "Sensor based on piezoresistive microcantilever technology", *Sensors and Actuators*, 88:47-51 (2001).
Porter, T.L. et al., "The Interaction of Biological Molecules with Clay Minerals: A scanning force microscopy study", *Scanning*, 22:1-5 (2000).
Vinayagam, A. et al., "DSDBASE: a consortium of native and modelled disulphide bonds in proteins", *Nucleic Acids Research Database Issue*, 32:D200-202 (2004).

* cited by examiner

MICROSENSOR MATERIAL AND METHODS FOR ANALYTE DETECTION

CROSS-REFERENCE TO RELATED APPLICATIONS

This application is a U.S. National Stage of International Patent Application No. PCT/US2008/000672, filed Jan. 18, 2008, which claims the benefit of U.S. Provisional Application No. 60/881,754, filed Jan. 19, 2007, and U.S. Provisional Application No. 60/926,474, filed Apr. 27, 2007, all of which are hereby incorporated by reference.

TECHNICAL FIELD

The present subject matter relates to compositions and methods for detecting chemical or biological analytes, and to relate to sensors using the compositions. More particularly, the subject matter relates to a polymer-particle sensor in which analytes compete with the polymer for interaction with the particles, and the presence of analyte results in a detectable change in the free volume of the polymer.

BACKGROUND

Chemical or "analyte" sensors typically employ a sensing component that is physically or chemically modified in the presence of an analyte. Such sensors include resistance/conductivity sensors, which are generally known as chemiresistors; optical sensors, surface acoustic wave sensors (SAWS), microelectromechanical system (MEMS) sensors, and other types of sensors.

One large class of analyte sensors are the chemiresistor sensors or "chemiresistors." The general principles behind chemiresistors were demonstrated as early as 1986, when metal ion-phthalocyanine films spread on the surface of interdigitated electrodes showed a change in resistance in response to organic analyte vapor. Charge flowed more easily when atoms in the sensor were brought together and less easily when the atoms were moved apart, which was accomplished by reversibly "swelling" the sensor with analyte or "shrinking" the sensor by removing analyte. Swelling and shrinking alter physical characteristics of the sensor, which produce a detectable change in the electrical conductivity/resistance of the sensor.

More recent analyte sensors contain organic polymers. Analytes typically diffuse into the polymer matrix, thereby changing the conductivity of the polymer by swelling or contracting the matrix and changing the distance between conductive atoms or the pathway taken by the mobile charge. The conductivity of such sensors can be increased through the addition of a "doping" agent into the matrix, such as a conductive salt or carbon black residue (as used in the past) to increase the charge carrying ability of the polymer. Other useful materials include dielectric plasticizers. Organic polymer-based sensors are described in, e.g., Lonergan et al. ((1996) *Chem. Mater.* 8:2298-2312) and Doleman et al. ((1998) *Anal. Chem.* 70:4177-90).

In particular examples, a polyaniline polymer doped with carbon black has yielded a class of chemiresistor detectors able to sense amine groups at a sensitivity 1 million-fold greater than that of the human olfactory system (Sotzing et al. (2000) *Chem. Mater.* 12: 593-595). A polyethylene oxide polymer chemiresistor doped with lithium perchlorate was shown to accurately detect and differentiate between the nerve gas simulants diisopropylmethylphosphonate (DIMP), dimethylformamide (DMMP), and dimethylmethylphosphonate (DMF) (Hughes, et al. (2001) *J. Electrochemical Society* 148:1-8). Organic polymer-inorganic particle sensors have used in a variety of applications, including those described in U.S. Pat. No. 5,571,401 and the internal references therein.

While conventional sensors often perform adequately for their intended uses, they are not ideally suited to all applications. The repeated expansion and contraction of the sensor matrix due to the influx and efflux of analytes weakens the sensor matrix and leads to reduced performance and eventual failure. It is also difficult to obtain sensors having uniform thin films of a matrix, which leads to variability among sensors. Thick films are generally undesirable because they require an extended period of time to absorb the target analyte, thus increasing the amount of time required for a response to an analyte.

The need exists for more robust and more sensitive analyte sensors. A particularly urgent need exists to rapidly and selectively detect toxic gases, such as hydrogen cyanide, chlorine, carbon monoxide, and hydrogen sulfide, which are volatile chemicals that can rapidly cause death or disability even at low levels of exposure.

BRIEF SUMMARY

The following aspects and embodiments thereof described and illustrated below are meant to be exemplary and illustrative, not limiting in scope.

In one aspect, a composition is provided, the composition comprising a finely divided solid material dispersed in a substantially linear polymeric material having a free volume, the polymeric material capable of interacting with the solid material to reduce the free volume of the polymeric material, the interaction being reduced by the presence of analyte, wherein upon exposure to an analyte, the analyte competes with the polymeric material for interaction with the solid material, producing a detectable change in the free volume of the polymeric material.

In some embodiments, the analyte is in a gas phase. In another embodiment, the analyte is a noxious gas.

In some embodiments, the volume change is an increase in volume. In particular embodiments, the volume increase is an increase in the free volume of the polymer.

In some embodiments, the polymeric material and solid material interact via covalent bonds. In particular embodiments, the polymeric material and solid material interact via disulfide linkages.

In some embodiments, the polymeric material includes at least one chemical moiety selected from the group consisting of sulfides and amines.

In some embodiments, the polymeric material is a polypeptide. In particular embodiments, the polypeptide is a naturally-occurring fibrous protein. In particular embodiments, the polypeptide is keratin. In particular embodiments, the polypeptide is cysteine-rich polypeptide.

In other embodiments, the polymeric material is a thiol-containing acrylic polymer, such as polymercaptoacrylate.

In some embodiments, the solid material is a metal. In particular embodiments, the metal is a noble metal. In particular embodiments, the metal is gold.

In other embodiments, the metal in nickel.

In some embodiments, the analyte is selected from HCN, HF, phosgene, CO, and $CO_2$.

In another aspect, a method for detecting the presence of analyte using a compositon as described above is provided. The method comprises providing a sensor material as described above, where the polymeric material has a free volume that is reduced upon interaction with the solid material and increased when the interaction with the solid material is reduced, exposing the sensor material to the analyte, which analyte competes with the polymeric material for interaction with the solid material, thereby reducing the interaction between the polymeric material and the solid matrix and increasing the free volume of the polymeric material, and detecting the increase in the free volume of the polymeric material. The increase in the free volume of the polymeric material corresponds to the presence of the analyte.

In some embodiments, the chemical bonds are covalent bonds. In particular embodiments, the covalent bonds are disulfide linkages.

In some embodiments, the polymeric material includes at least one chemical moiety selected from the group consisting of sulfides and amines. In particular embodiments, the polymeric material is a polypeptide. In other embodiments, the polymeric material is polymercaptoacrylate.

In some embodiments, the solid material is a metal.

In another aspect, a sensor comprising a composition as set forth above in provided. The sensor, in one embodiment, includes a microcantilever on which the composition is deposited, the microcantilever having first and second opposing ends. One end of the microcantilever is secured to a base, and the opposing end is in contact with the sensing composition. In one embodiment, the opposing end is in contact by virture of the end being embedded in the composition, in another embodiment the opposing end is in contact with the composition by virtue of the composition being deposited on all or a portion of the microcantilever. The sensor includes the requisite electronics for detecting a change in or movement of the microcantilever when the composition is in the presence of an analyte.

In addition to the exemplary aspects and embodiments described above, further aspects and embodiments will become apparent by reference to the drawings and by study of the following descriptions.

DETAILED DESCRIPTION

Figure 1:
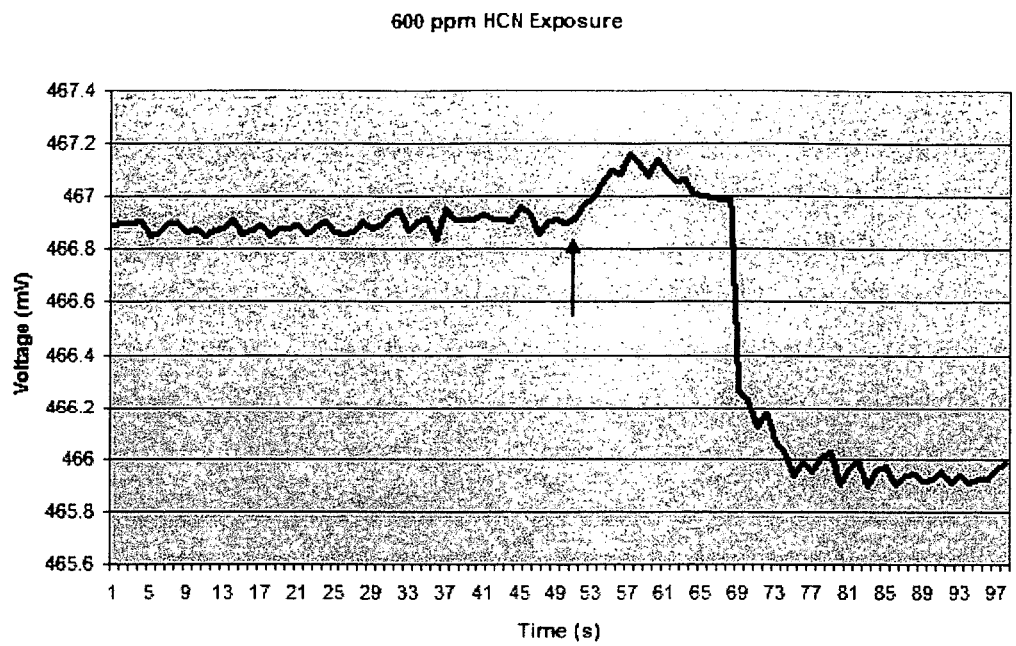
FIG. 1 is a graph showing the use of an embodiment of the present polymer-particle analyte sensor material for detecting HCN cyanide, obtained by the addition of $H_2SO_4$ to KCN. An embedded polymer microcantilever (EPM) sensor was used to detect the volumetric change in the sensor material. Movement of the cantilever arm away from the sensor material results in a decrease in voltage (Y-axis). The arrow indicates the time of addition of $H_2SO_4$ to evolve HCN gas.

The present compositions and methods relate to an analyte sensor comprising a polymeric material having particles dispersed therein to form a polymer-particle matrix. The polymer material interacts with the particles to restrict the free volume of the polymer material. Upon exposure to an analyte, the analyte competes with the polymer material for interaction with the particles, thereby reducing the amount of interaction between the polymer material and the particles, and increasing the free volume of the polymer material (see, e.g., Fox and Flory (1950) *J. Appl. Phys.* 21:581; Doolittle (1951) *J. Appl. Phys.* 22:1031; Simha and Somcynsky (1969) *Macromolecules* 2:342).

The increased free volume of the polymer results in a volumetric change in the polymer-particle matrix, which may be detected using e.g., a piezoresistive microcantilever. The change in volume of the polymer-particle matrix can be many times the volume of the analyte present, and the analyte specificity for the polymer-particle matrix can be selected and/or tailored by selection of polymer materials having different functional groups for interacting with the particles, and/or via selection of particles of different materials. Exemplary polymers and particle materials are set forth below.

Competition between the analyte and polymer material in the polymer-particle matrix for binding with the polymer-embedded particles is a feature that distinguishes the present compositions and methods from known chemiresistors and dendrimer analyte sensors, which rely on an analyte dissolving into the sensor polymer to produce detectable swelling. Polymer swelling is the manner by which Porter et al. detected organic vapors using polymers showing high solubility for organic solvents such as EVA, PIB, and the like (Koser et al. (2004) *Senors and Actuators B: Chemical*, 99(2-3):474). Likewise, chemiresistors require an analyte to dissolve into the polymer to cause swelling that pushes apart conductive particles. In these conventional swellable polymer sensors, analytes typically produce a detectable change in the sensor matrix by producing a changing in the charge density of the sensor material or the conductivity of the sensor material. While the influx of analytes alters the physical characteristics of the sensor (including the electrical characteristics) the presence of analyte does not cause the breaking of bonds between the polymer material and the particles.

The present composition, also referred to as an analyte sensing material, allows the rapid detection of analytes having limited or no solubility in the matrix polymer. Instead of "swelling" the matrix polymer, analytes produce a detectable signal in the present sensors by disrupting specific bond between the matrix polymer and a nanoparticle. These bonds are broken in the presence of analyte and formed when analyte is removed.

Without being limited to a theory, it is believed that the volumetric change or shift in the sensing material is due, at least in part, to the increased free volume of the polymer in the presence of analyte, which reversibly competes with the polymer for interactions with the particle. While it is possible that some portion of the volume change may be due to diffusion of the analyte into the sensing material, "probe-target" binding on the material surface or bulk, or surface or bulk chemical reactions between the analyte and the sensing material, it is primarily the reversible interaction between the polymer matrix and particles that confers sensitivity and selectivity to the present sensors.

These interactions are generally determined by the functional groups present on the polymer matrix and the particles present in the sensor material. The bonds may be covalent bonds. In particular embodiments, the bonds may be hydrogen bonds or electrostatic bonds. The bonds may be of the same type throughout the sensor material. Alternatively, sensor materials and particles may interact through several different types of bonds.

The volume change in the sensor material can be accurately detected using, e.g., an embedded piezoresistive microcantilever (EPM) sensor. Such sensors can measure movement of only a few angstroms. Sensor material present in a cantilever sensor may be referred to a "transducer" or "transducer element."

Examples of the present compositions and methods are described in further detail, below.

I. Polymers and Functional Groups

Polymers for use with the present compositions and methods include both naturally-occurring polymers and synthetic polymers. Naturally-occurring polymers include but are not limited to polypeptides, polynucleotides, carbohydrates, glycogen, and/or derivatives, thereof. One exemplary polypeptide is keratin. Substantially linear polymers are preferred, although a moderate amount of branching (e.g., less than 10 branches per molecule, less than 6 branches per molecule, less than 4 branches per molecule or even less than 2 branches per molecule) are suitable. Extensive branching, as found in dendrimeric polymers (or dendrimers), stabilizes polymer free volume independent of the presence or absence of particles. Accordingly, the use of dendrimeric polymers is inconsistent with the functioning of the present sensor.

In selecting a polymer for use with the present compositions and methods, an important consideration is the type or types of functional groups present on the polymer, which interacts with the particles. In some embodiments, the functional groups on the polymer matrix are sulfhydryl (SH) groups, which can spontaneously form thiolate bonds in the presence of a metal particle, such as a gold particle. Sulfhydryl groups are readily produced by reducing disulfide bonds between cysteine residues in a polypeptide or between different polypeptides. Cysteine-rich polypeptides are well-suited for interacting with particles because each polypeptide polymer can form numerous (e.g., more than 20, more than 40, more than 60, or even more than 80) disulfide bonds with particles.

Disulfide-bond containing polypeptides are known in the art, and many are described in DSDBASE, a database of disulfide-containing proteins available from the National Centre for Biological Sciences (NCBS) (Vinayagam et al. (2004) *Nucleic Acids Res*. 32:D200-202; http://caps.ncbs.res.in/dsdbase//dsdbase.html, last accessed Feb. 12, 2007). CysView is a program that identifies and classifies proteins based on their disulfide bond linkages (Lenffer et al. (2004) *Nucleic Acids Res*. 32:W350-355; http://research.i2r.a-star.edu.sg/CysView/, last accessed Feb. 12, 2007). Disulfide-bond containing polypeptides include but are not limited to hydrolases, oxidoreductases, transferases, hormones, toxins, and protein involved in blood clotting, cell adhesion, cell-cell recognition, and cell defense (Lenffer et al. (2004) *Nucleic Acids Res*. 32:W350-355; Hartig et al. (2005) *Protein Sci*. 14:474-82).

In other embodiments, polypeptides having a lower cysteine composition may be preferable, e.g., in a sensor medium where fewer disulfide bonds with the particles are an objective, or where the polypeptides interact with the particles via the nitrogen atoms of the histidine imidazole ring or via the carbonyl oxygen or the amide nitrogen of the amide group in the peptide backbone. Terminal amino groups, deprotonated amide and carboxylate groups, and thioether groups can also be used to attach metal particles. Amino groups generally do not spontaneously attach to metal particles, but readily attach to modified particles, such as particles modified with a carboxylic acid-terminated thiol group. Polypeptides-metal conjugates are described, e.g., in U.S. Patent Pub. No. 20060293510.

In some embodiments, preferred naturally occurring polypeptides for use in the sensor material are fibrous proteins, exemplified by the structural proteins keratin and collagen. Fibrous proteins are generally elongated molecules dominated by a single secondary structure motif. The rigid structure of fibrous proteins means that such polymers have a preferred secondary structure which can be perturbed through interactions with particles. Breaking the interactions with the particles (e.g., in the presence of an analyte) allows the fibrous polypeptides to return to their original structure and free volume. In this manner, the polymers have detectably different free volumes in the presence and absence of particles. In contrast, flexible polypeptides (e.g., globular proteins) are less likely to return to their natural secondary structure and free volume upon being released from particles. In such cases, the difference in free volume in the presence or absence of particles is likely to be less.

In one embodiment, the naturally-occurring polymer is an abundant and readily obtainable fibrous polypeptide, such as keratin, which is described for use in making a hydrogen cyanide sensor in Examples 1-3. Keratins are members of the coiled coil family of structural proteins, and are found in hair, wool, feathers, nail, horns, and other epithelial coverings. In many cases, keratins comprise up to about 50% of the dry weight of such anatomical structures. Keratin fibers consist of bundles of coiled-coils of the polypeptide α-keratin, of which there is an acidic form and a basic form. α-keratin polypeptide have a repeating sequence of mostly polar amino acid residues (mainly Lys, Arg, Asp, and Glu), which interact with oppositely-charged residues on adjacent α-keratin polypeptides.

The amino acid composition of keratin is about 20% cysteine, allowing the formation of intermolecular disulfide bonds between one or more adjacent α-keratin polypeptides. Most cysteine residues are located at or near the terminal regions of the protein. Reduced keratins, in which some or all of the S—S bonds are reduced to free sulfhydryl (SH) groups, are readily formed by the addition of a reducing agents, such as 2-mercaptoethanol. The reduced SH groups are reactive species that spontaneously form thiolate bonds in the presence of a particle, such as a gold particle, which is capable of sharing electrons. The resulting keratin-particle matrix is thereby stabilized by disulfide bonds between the polymer matrix and the particles, which reduce the free volume of the polymer.

While the use of keratin is exemplified, other polypeptides are expected to work in the present compositions and methods. For example, collagen is a coiled-coil protein found in skin, connective tissues, bone, teeth, and cartilage. Collagen fibers consist of three left-handed helical polypeptides having a repeating sequence in which nearly every third amino acid residue is glycine. Prolines and lysines in collagen polypeptides are frequently post-translationally hydroxylated and may include sugar groups. Three collagen polypeptides together form a right-handed superhelical coiled-coil structure. The amino acid composition of collagen is 15-30% 3-hydroxyproline, 4 hydroxyproline and, and 5-hydroxylysine, and about 30% glycine.

Other polypeptides (or derivatives, thereof) for use according to the present compositions and methods include but are not limited to elastin, silk, fibronectin, laminin, tubulin, actin, myosine, glycosaminoglycans, and proteoglycans. Such polypeptides (or the polypeptide components, thereof) may be modified to increase rigidity. Polypeptides comprising repeating sequence motifs, hydroxylated prolines and/or lysine residues, high glycine content, high cysteine content, high content of Lys, Arg, Asp, and or Glu) a large amount of secondary structures such as helices and β-sheets, coiled coil polypeptides, and other feature associated with structural protein, are also suitable for use in the present compositions and methods.

The selection of a particular polypeptide, may be used to "tune" the sensor material, e.g., by increasing or decreasing the number and type of interactions between the polymers and the particles and/or increasing or decreasing the difference between the free volume in the presence and absence of particles.

Polypeptides may be obtained from natural sources (e.g., wool, in the case of keratin), may be synthesized (e.g., in a peptide synthesizer), or may be expressed in cells (e.g., bacteria, yeast, mammalian, or insect cells), using methods known in the relevant arts. Recombinant polypeptides can be designed with any number of cysteine or other residues for interacting with particles. Homopolymeric polypeptides, or polypeptides containing only a subset of amino acid residues may also be used.

In other embodiments, the polymer is a nucleic acid or nucleic acid derivative. Organothiol nucleic acid-metal conjugates are described in, e.g., U.S. Pat. No. 5,728,590. The reactive group on the nucleic acid that is used to bond to the particle are preferably an amino group, an aldehyde group, an epoxy group, or a carboxyl group (see, e.g., U.S. Pat. No. 6,664,051). Amino groups are present in naturally-occurring nucleic acids, e.g., in the bases adenine, guanine, and cytosine. Amino groups can be attached to particles via electrostatic bonds, or using a silane-coupling agent or carboxylic acid-terminated thiol group attached to the particle. Examples of the silane-coupling agents are γ-aminopropyltrimethoxysilane, N-β(aminoethyl)-γ-aminopropyltrimethoxysilane, and N-β(aminoethyl)-γ-aminopropylmethyldimethoxysilane.

Particles may be modified with a mixed organic/inorganic zirconium phosphonate monolayer film to provide a bonding partner for nucleic acids terminated with phosphates. The method results in the specific binding of terminal phosphate groups with minimal binding of internal phosphodiesters group. In preferred embodiments, each polynucleotide molecule forms multiple bonds with particles.

In some embodiments, a double-stranded or partially double-stranded nucleic acid is used, such as dsDNS, dsRNA, or heteroduplex DNA/RNA. The partial double-stranded nature of such polynucleotides increases their rigidity and increases the different between free volume in the presence and absence of particles. In particular embodiments, binding of the nucleic acid to the particles involved partial denaturation of the nucleic acid, with renaturation occurring when the nucleic acids are released from the particles (e.g., by the presence of analyte). For the purposes of the present description, plasmid or other episomal nucleic acids are considered "linear" polymers, even though they are technically closed circles.

Other polymers for use in the present compositions and methods include, polyamines, polyamides, polyimides, polycarbonates, polyurethanes, polyacrylonitrile, polyacrylic acid, polyacrylates, polyacrylamides, polyphosphazenes, polyvinyl alcohol, polyvinyl chloride, heterocyclic polymers, polyesters, modified polyolefins, polyacetylene, aromatic polymers, poly(p-phenylene), poly(phenylene vinylene), polyaniline, polythiophene, poly(phenylene sulfide), polypyrrole and copolymers and derivatives thereof; polysilanes and polysiloxane polymers, such as poly(dimethylsiloxane) (PDMS), carbohydrates, and glycogen. Such polymers may be modified with any number of functional groups, or chemical moieties, to mediate binding to particles. Exemplary groups are thiol and amino groups. In one embodiment, the polymer polyethylene oxide is excluded from the polymers contemplated for use. An exemplary acrylate polymer is polymercaptoacrylate, which is described for use in making a carbon monoxide sensor in Example 4.

Other polymers will be apparent to one skilled in the art without departing from the spirit of the present compositions and methods.

II. Particles

The sensor material includes a finely divided solid material, preferably in the form of finely divided particles. The phrase "finely divided" as used herein intends a particle having a diameter of between about 1-1,000 nm (10-10,000 Angstroms). In another embodiment, preferred particles have an average diameter of less than about 800 nanometers (nm) and preferably from about 1 nm to about 800 nm, more preferably of from about 2 nm to about 750 nm, or from about 10 nm to about 500 nm. Particle diameter may be determined by transmission electron microscopy or other methods known in the art. The collection or plurality of particles dispersed in the sensor material may contain particles of a uniform size or of different sizes. Sensor materials may also contain particles made of a single material, particles made of two or more different materials, or different particles made of two or more different materials.

An exemplary material for use as the particles is a material that has a large number of electrons available for bonding, as in the case of a metal material. Metals include the Group 1A (alkali) metals (i.e, Li, Na, K, Rb, Cs, and Fr), the Group 2A (alkaline earth) metals (i.e., Be, Mg, Ca, Sr, Ba, and Ra, the first row transition metals (i.e., Sc, Ti, V, Cr, Mn, Fe, Co, Ni, and Cu), the second row transition metals (i.e., Y, Zr, Nb, Mo, Tc, Ru, Rh, Pd, Ag, and Cd), the third row transition metals (i.e., La, Ce, Pr, Nd, Pm, Sm, Eu, Gd, Tb, Dy, Ho, Er, Tm, Yb, Lu, Hf, Ta, W, Re, Os, Ir, Pt, Au, and Hg), the fourth row transition metals (i.e, Ac, Th, Pa, U, Np, Pu, Am, Cm, Bk, Cf, Es, Fm, Md, No, Lw, etc.), the Group 3A metals (i.e., Al, Ga, In, and Tl), the 4A metals (i.e, Sn and Pb), the Group 5A metal, Bi, and even metalloids, such as B, Si, Ge, As, Sb, Te, Po, and At. In some embodiments, the metal is a noble metal, such as Pd, Pt, Au, or Ag. Gold particles are readily available and their use is exemplified, herein.

Particles may be made of metal alloys (e.g., Pt—Pd), metals coated on ceramic, glass, or other substrates, metals coated on shaped particles (e.g., spherical, hollow, elongated, etc.), or other variations and combinations. Particles may also contain metal salts, particularly for interaction with a polymer having charged functional groups or polar polymers.

Suitable particles may also be made of inorganic materials such as molecular sieves, mica, wollastonite, calcium carbonate or similar insoluble materials.

Particles may be modified to facilitate and/or modulate interactions with the functional groups of the polymer. In some embodiments, the particles are modified with sulfide groups. Such sulfides may form disulfide linkages along with sulfides of the polymer. Sulfides may additionally or alternatively form disulfide linkages with sulfides of a linker molecule, to which the polymer forms bonds. The linker may contain a sulfide moiety and a functional group suitable for forming a linkage with the polymer. The polymer and linker may be in an attached arrangement prior to introduction to the particle.

The particles may also be modified with a carboxylic acid-terminated thiol group, which reacts readily with amino groups, such as those present on many naturally-occurring and synthetic polymers. Other modifications include modification with SH-aminodextrans, an alkoxy group, an ester group, an acid anhydride group, etc.

Particles are commercially available, and/or can be formed, for example, by flame synthesis, combustion, sol gel approaches, or laser pyrolysis.

III. Analytes

Numerous analytes may be detected using the present devices and methods. In a preferred embodiment, the sensor is used for detection of a noxious substance, which intends a liquid or gaseous substance that, when dispersed in the atmospher, irritates or injures organs and tissues of the human body or causes nausea. In a preferred embodiment, the noxious substance is a gaseous noxious substance. Substances capable of being noxious, particularly when in a gaseous state, include, but are not limited to, hydrogen fluoride (HF), carbon monoxide (CO), hydrogen sulfide ($H_2S$), phosphene ($PH_3$) and chlorine.

Other examples of substances contemplated for detection using the compositions and methods include noxious substances in addition to toxic substances and non-toxic substances. These substances include, but are not limited to, acetic acid, acetone, acrolein, acrylonitrile, acetylene, aldehydes, ammonia, arsine, benzene, boron trichloride, boron trifluoride, carbon disulfide, diborane, dimethylamine, dimethylhydrazine, dichlorosilane, disilane, ethanol, ethylene oxide, formaldehyde, hydrogen, hydrogen bromide, hydrogen chloride, hydrogen iodide, methanol, methyl mercaptan, monomethylamine, nitric oxide, nitrogen dioxide, nitrogen trifluoride, nitrous oxide, oxygen, phosphine, silane, silicon tetrachloride, silicon tetrafluoride, sulfur dioxide, styrene, sulfur hexafluoride, sulfur tetrafluoride, trichlorosilane, trimethylamine, tungsten hexafluoride, trichloroethylene, tetrachloroethylene, toluene, toluene diisocyanate, trichloroethane, vinyl chloride, and others.

Merely for purposes of illustrating the present materials, sensors, and methods, examples are set forth herein where hydrogen cyanide (HCN) is detected. HCN is a colorless gas with a "bitter almond" smell, although many people do not detect any odor associated with HCN. Human exposure may occur by breathing air containing HCN gas, drinking water contaminated by cyanide, or through skin contact. HCN gas has been used as in terrorism, being particularly easy to produce and release into an enclosed space, where it is noxious to humans and animals.

Following exposure, the cyanide ($CN^-$) ion forms a complex with the respiratory cytochrome oxidase enzyme system, interfering with oxygen utilization by cells of the body (see, e.g., Way (1984) *Ann. Rev. Pharmacol. and Toxicol.* 24:451-481; Peddy et al. (2006) *Pediatric Crit. Care Med.* 7:79-82; Baskin (2002) *Military Phychol.* 14:159-177). As organs with high rates of aerobic metabolism, the heart and brain are particularly susceptible to the harmful effects of HCN.

Symptoms of exposure to HCN (i.e., cyanide poisoning) include convulsions, respiratory distress or failure, loss of consciousness, and ultimately death. These symptoms, and their severity, depend on the concentration/dose and exposure time. In this case of high-dose, lethal exposure, symptoms of cyanide poisoning may be evident in as little as 15 seconds, with death occurring in 10 minutes. Higher HCN concentration levels produce a more rapid onset of symptoms, for example, exposure to 500 ppm HCN gas result in death within about 15 minutes, while exposure to 100 ppm HCN results in death within about one hour.

Cyanide exposure may also occur upon exposure to cyanide salts, such as sodium and potassium cyanide. HCN is released from NaCN and KCN upon contact with moisture and particularly upon contact with stomach acid. This form of administration is common in the case of "suicide pills" or "cyanide capsules." In some embodiments, the present compositions and methods are for detecting HCN gas released from solid cyanide forms, e.g., upon exposure to acid.

Protective gear and breathing apparatus are needed for HCN concentrations of approximately 50 ppm or greater. The present compositions and sensor provide for detection of HCN when present at a concentration of at least about 1 ppm, preferably when present at concentrations of at least about 10 ppm, 50 ppm, 100 ppm, or 500 ppm or greater.

In some embodiments, the analyte for detection using the compositions and sensor described herein is a plurality of analytes, which may be selected from any of the analytes identified herein or known in the art. In one example, the analytes are HCN and phosgene. In another example, the analytes are a plurality of gases used in semiconductor manufacturing. In another example, the analytes are a plurality of sulfide-containing analytes.

As noted above, the analyte or analytes to be detected need not be soluble in the polymer matrix. For example, the equilibrium solubility of the analyte in the matrix polymer may be less than 25%, less than 15%, less than 10%, or even less than 5%. Equilibrium solubility may be measured by contacting the matrix polymer, in the absence of a solid particle, with an excess of the analyte and measuring the equlibrum percent weight gain.

IV. Piezoresistive Microcantilever Sensors

Embedded piezoresistive microcantilever (EPM) sensors provide a small, low-cost and simple platform for the rapid detection of small movements. These sensors are sufficiently sensitive to detect the swelling of a sensor material in response to an analyte. EPM sensors are generally microelectromechanical system (MEMS) devices consisting of a piezoresistive microcantilever that can be partially embedded in, or placed on the surface of, a sensing material, including those described herein. The EPM sensor, therefore, produces a measurable response (e.g., in terms of electrical properties) to the volumetric change in the sensor material when it is exposed to an analyte.

EPM sensors have been suggested for use in a variety of sensing applications involving different analytes. Such applications include detecting volatile organic compounds (VOCs) (Porter et al. (2000) *Scanning* 22:1-5; Porter et al. (2003) *Ultramicroscopy* 97:365-369), detecting chlorinated hydrocarbons (e.g., in a water and vapor phase), detecting personal hydration levels (Gunter et al. (2005) *Med. Eng. Phys.* 27:215-220), detecting carbon monoxide gas (Kooser et al. (2004) *Sens. Actuators B*99:430-433), detecting single-strand DNA (Gunter et al. (2004) *I.E.E.E. Sensors* 4:430-433), detecting proteins (Kooser et al. (2003) *Biosens. Bioelectron.* 19:503-508), and detecting viruses (Gunter et al. (2003) *Sens. Actuators A*107:219-224).

Exemplary microcantilever-based sensors may operate as static coated devices (Baselt et al. (1996) *J. Vac. Sci. Technol.* 14:789-793; Thundat et al. (1994) *Appl. Phys. Lett.* 64:2894-2896), vibrating cantilever devices (Thundat et al. (1995) *Anal. Chem.* 67:519-521), contact-mode devices (Porter et al. (2001) *Sens, Actuators A*88:47-51; Porter et al. (2000) *Scanning* 22:1-5), or embedded sensors (Porter et al. (2003) *Ultramicroscopy* 97:365-369). In addition, both standard (inert) and piezoresistive cantilevers can be used. The cantilever may be embedded or partially embedded into a sensing material to "pre-load" the sensor.

Electronics for EPM sensors are capable of measuring the cantilever resistance during a sensing event. Such sensors are known in the art and exemplified by microcantilevers described in U.S. Pat. Nos. 6,523,392, 6,823,717, and 6,854,371, and U.S. Patent Pub. Nos. 2005/0164299 and 2006/0053871, which are incorporated by reference herein. In one embodiment, a single-chip AD7793 24-bit A-D converter, which functions as a 6½ digit multimeter, may be used to directly measure the cantilever resistance. In another preferred embodiment, a Wheatstone bridge (with the cantilever occupying one arm of the full-bridge) coupled to an instrumentation amplifier and an A-D converter may be used to directly measure the cantilever resistance.

Another preferred embodiment of the EPM sensor may be in a miniaturized sensor-electronics package, including integration of the package into a multi-hop wireless network of "motes". The combination of small, simple EPM sensors with battery powered wireless motes may eventually find worthwhile field applications in the sensing of many analytes, including poisons such HCN or other dangerous or environmentally important chemicals or vapors.

In one embodiment relating to the present compositions and methods, a microcantilever sensor was used to measure the free volume change of a sensor material. This embodiment utilizes a sensor material made of a keratin polymer matrix attached to gold nanoparticles via disulfide linkages. The polymers were attached by functionalizing the particles with thiol groups, and then forming disulfide bonds between the polymer and particle by reducing the disulfide bonds, then oxidizing the bonds of the pre-mixed polymers and particle. When this sensor is exposed to 150 ppm HCN and 600 ppm HCN, the microcantilever device detects the change in sensor material volume within seconds. The response to HCN is measured as a decrease in sensor voltage. While the above-described EPM sensor provided good results, other microcantilever-based sensors can be used with the present compositions and methods.

V. Exemplary Sensing Composition and Sensor

In a working example in support of the present compositions and methods, a polymer-particle sensor material was used in combination with an EPM sensor to detect HCN gas evolved upon adding acid to a cyanide salt. Preparation and testing of the EPM device is described in Examples 1-3. Movement of the cantilever arm away from the sensor material, as in the case of a volumetric increase of the senor material, results in detectable resistance in the EPM device, which in this case was detected as a reduced voltage.

FIG. 1 shows the response of the sensor material following exposure to about 600 ppm HCN. The arrow indicates the time (49 seconds) at which $H_2SO_4$ was dropped into KCN powder to evolve HCN gas. Within a few seconds, the sensor voltage initially rises. Approximately 20 seconds following this increase voltage, the sensor voltage decreases, leveling off about 25 seconds following the addition of $H_2SO_4$. The cantilever voltage decreased to well below the starting level, indicating that the cantilever was bending away from the sensor material, consistent with a volumetric increase of the sensor material. The net voltage change from the initial reading to the final reading was approximately 1 mV (i.e., about 467 mV-466 mV). Given a cantilever sensitivity of approximately 4.7 Ω/μm, the estimated net cantilever deflection (based on current measurement) from the initial position to the final position was 1 μm.

The subsequent exposures to similar amounts of HCN resulted in no sensor response, suggesting that at such a high concentration of HCN, the sensor acted as a chemical fuse that provided a one-time signal.

The initial rise in sensor voltage following exposure to HCN suggests that the cantilever may have "unloaded" some of the initial "pre-load" (pre-strain) introduced during the assembly of the sensor, corresponding to the cantilever bending back toward (or into) the sensor material. This type of cantilever response to the HCN analyte, i.e., in which the initial response is reduced deflection, followed by a subsequent larger increased deflection, has been observed by previously in systems that respond rapidly to analytes (Gunter et al. (2005) *Med. Eng. Phys.* 27:215-220). There is no adequate explanation for this behavior, as it is not predicted by standard models describing the diffusion or partitioning of analyte molecules into a polymer or other host matrices (Cussler (1997) Cambridge University Press).

Without being bound to theory, it is postulated that two separate events are occurring. First, a rapid response event, which may largely be confined to the surface of the sensing material, may initially be occurring. The initial response may be due to adsorption, absorption, or rapid protonation of the keratin by the HCN. Keratin disulfide cross-links may also be broken. These responses may represent a rapid "melting" of the material in the top-most layers of the sensing material. Second, a slower, and ultimately larger response may be due to the bulk diffusion of the analyte into, and subsequent chemical reaction of the HCN molecules with, the particles, thereby displacing the keratin polymer and increasing the free volume of the sensor material. The proposed reaction is:

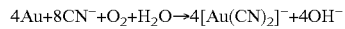

Figure 2:
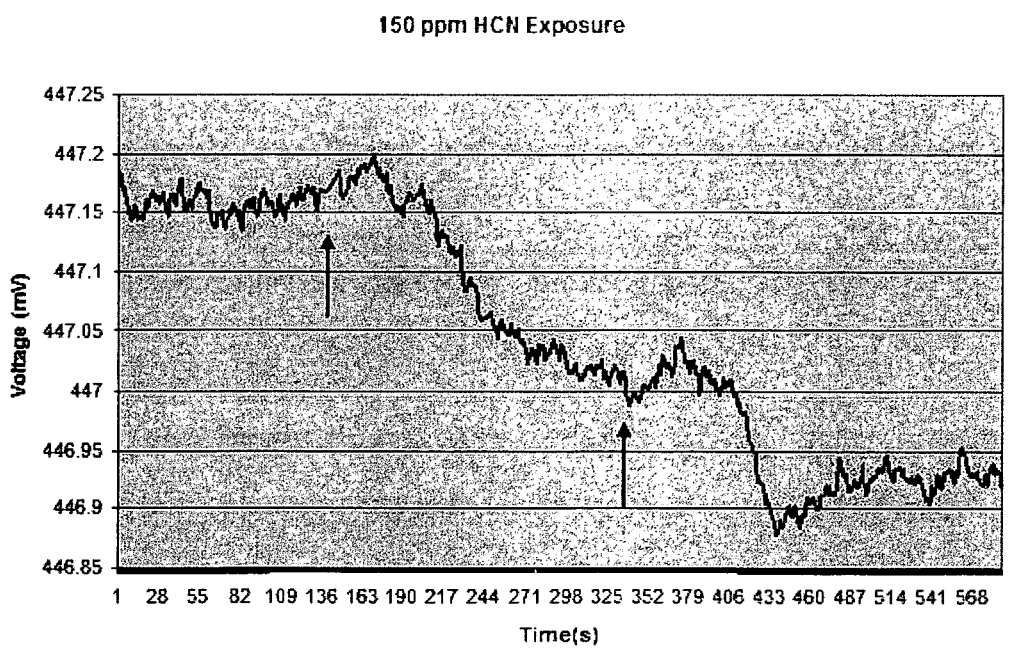
FIG. 2 is a graph showing the use of an embodiment of the present polymer-particle analyte sensor material for detecting two consecutive exposures to approximately 150 ppm HCN, obtained by the addition of $H_2SO_4$ to KCN at two different times (arrows).

As shown in FIG. 2, EPM sensors were also able to detect an HCN exposure of approximately 150 ppm. As indicated by the arrows, the first addition of $H_2SO_4$ to KCN was at 139 seconds, as indicated by the first arrow. As with the earlier exposure, the initial sensor response was an increase in voltage. This initial increase was followed by a decrease in sensor voltage. Note that the time frame of the 150 ppm-exposure is about 210 seconds, which is approximately 5 times that of the previous 600 ppm-exposure. Despite the increased time required at lower HCN exposure, the reaction time of the sensor was still fairly short.

The net voltage change from initial reading to final reading was approximately 0.15 mV, or ⅙ of the previous 600 ppm-voltage response. The estimated net cantilever deflection from prior to exposure to end was 0.16 μm. It is expected that the net cantilever response for the 150 ppm exposure would be approximately ¼ of the response of the 600 ppm exposure instead of ⅙. Since the present sensors are assembled by hand, there may be small variations from one sensor to the next in sensing material layer thickness, in microcantilever pre-straining, and in percent of cantilever length that is embedded in the sensing material.

The same sensor and sensor material were exposed a second time to 150 ppm HCN at 335 seconds, as indicated by the second arrow on FIG. 2. Here, the sensor was able to react a second time to the presence of HCN, indicating that the first exposure to 150 ppm did not "exhaust" the detection capability of the sensor material. The second net sensor voltage response was approximately 0.1 mV, or about 35% less than that of the first exposure.

Figure 3:
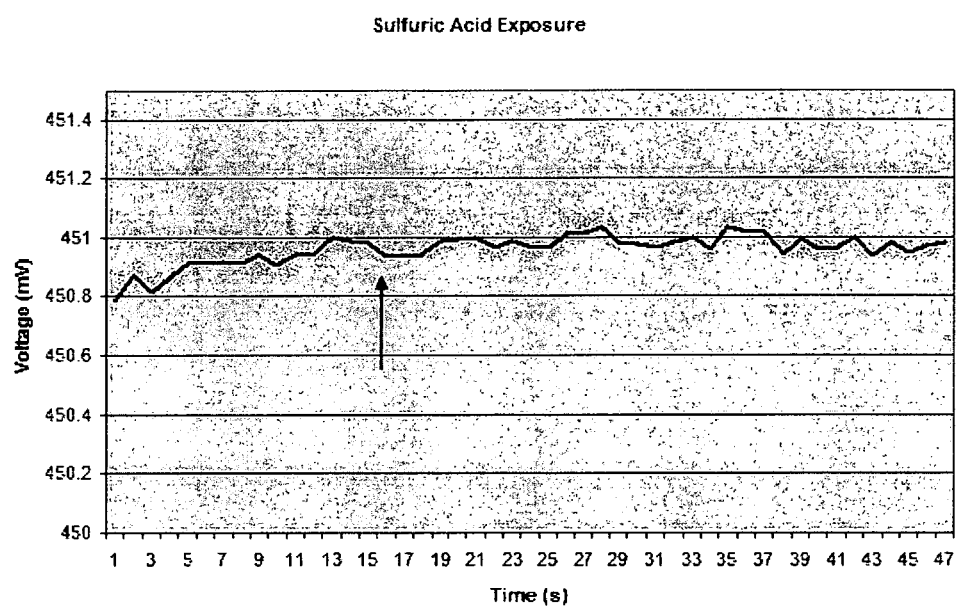
FIG. 3 is a graph showing the results of exposing an embodiment of the present polymer-particle analyte sensor material to $H_2SO_4$ in the absence of KCN. The arrow indicates the time of addition of $H_2SO_4$.

The same EPM sensor used in the experiment of FIG. 2 was exposed to $H_2SO_4$ vapors only, in the absence of KCN (FIG. 3). The arrow indicates the time at which the acid was introduced to a chamber including the sensor device. The amount of $H_2SO_4$ vapor was similar to that used in the higher concentration HCN (i.e., 600 ppm) experiment, described above and in the Examples. As shown in FIG. 3, $H_2SO_4$ by itself had no significant effect on the sensor or sensor material, demonstrating that in the previous experiments the sensor material responded to HCN.

These described results are reproducible across other sensors. HCN detection signals currently vary 10-20% from one sensor to the next. Since the present sensors are assembled by hand, there are unavoidable variations among sensors, e.g., in sensing material layer thickness, in microcantilever pre-straining, and in percent of cantilever length that is embedded in the sensing material. Automated production will likely improve reproducibility.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

VI. Utility

Fields in which the demand for robust, portable, and sensitive analyte sensors for volatile gas detection include those relating to environmental studies, medicine, and counterterrorism.

Early detection of organic molecules when spilled or accidentally released into the environment can minimize damage and expedite cleanup procedures and the ability to detect nerve gases or other volatile/toxic gases in public buildings and transportation areas by reliable sensing equipment has become of increased importance.

The ability to detect biogenic amines would aid medical personnel in the diagnosis of disease. For example, biogenic amines such as aniline and o-toluidine have been reported as biomarkers for lung cancer, while di and tri-methylamines have been reported as the cause of the fishy uremic breath observed by patients with renal failure. Early detection of such amine groups would expedite diagnosis and treatment. This technology could also allow for the diagnosis of diseases or conditions in patients living in areas without proper health care, including remote areas and places not readily accessible.

The foregoing examples of the related art and limitations related therewith are intended to be illustrative and not exclusive. Other limitations of the related art will become apparent to those of skill in the art upon a reading of the specification and a study of the drawings.

EXAMPLES

The following examples are illustrative in nature and are not intended to be limiting. The following definitions are provided for clarity. Abbreviations not specifically defined should be accorded their ordinary meaning as used in the art.

| | |
|---|---|
| M | molar |
| mM | millimolar |
| nM | nanomolar |
| m | meter |
| mm | millimeter |
| μm | micrometer |
| nm | nanometer |
| Ω | Ohm |
| kΩ | kiloOhm |
| ppm | parts per million |
| V | Volt |
| mV | milliVolt |
| g | gram |
| °C. | degrees Celsius |
| mOsmol | milliosmolarity equivalents |

Example 1

Sensor Material to Detect Hydrogen Cyanide

An exemplary sensing material was comprised of a kertain matrix in combination with thiolated colloidal gold particles. α-keratins assemble intermediate filaments by forming multiple disulfide cross-links among the molecules (Nelson and Cox (2005) *Principles of biochemistry*, W. H. Freeman and Co.). Alkanethiol monolayers form on gold surfaces by strong coordination of alkanethiol compounds to gold by self-assembly (Bain (1989) *J. Am. Chem. Soc.* 111:321-335; Nuzzo and Allara (1983) *J. Am. Chem. Soc.* 105:4481-4483; Whitesides and Laibinis (1990) *Langmuir* 6:87-96).

Keratin was mixed first with 2-mercaptoethanol to reduce disulfides to sulfhydryls, and then with colloidal gold to form a self-assembled matrix of nanogold-keratin via gold thiolate coordination. The source of keratin was VariKer 100 keratin powder (Variati and Company, Milan, Italy). Colloidal gold source was particles with a diameter of 20 nm in aqueous suspension (Sigma-Aldrich, St. Louis, Mo.). The keratin and colloidal gold were used in a 1:1 ratio, although other ratios can be used, to form a liquid phase sensing material.

The liquid phase sensing material was deposited onto glass substrates, and a sensor microcantilever was brought into contact with the use of a micromanipulator. The sensor microcantilever is as described in U.S. Pat. Nos. 6,523,392, 6,823,717, and 6,854,371. Only the last approximate ⅓ of the microcantilever length was brought into contact with the sensing material. This assembly process allowed the cantilever to be partially "embedded" in the sensing material after drying. The nominal length of the cantilevers was 200 μm, with a width of 40 μm. Each cantilever die also contained an integrated thermistor for temperature measurement; however the thermistor component of these dies was not used in the current experiments.

The nominal resistance of the bare cantilevers before assembly was 2.2 kΩ. After material deposition and drying, the finished sensors exhibited resistances of approximately 2.15 kΩ, indicating that the cantilevers have been pre-strained an amount equivalent to 50 kΩ, and in the instant case, strained in a direction upward (away) from the sensor substrate. The amount of pre-straining (or pre-loading) varied slightly from one sensor to the next, owing to the manual deposition and assembly process.

The sensors were tested in a chamber of approximately 11 liters in volume. Production of HCN in the chamber was achieved by exposing a measured amount of KCN powder to 96% sulfuric acid ($H_2SO_4$), which produced $K_2SO_4$ and HCN gas (about 600 ppm; FIG. 1).

This colloidal gold entrained in the keratin reacted with the HCN and the ambient moisture of keratin hydration as:

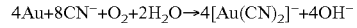

$$4Au+8CN^-+O_2+2H_2O \rightarrow 4[Au(CN)_2]^- +4OH^-$$

This coordination of cyanide to the entrained gold, with the resulting displacement of the polymers and increase of their free volume, produced a measurable displacement of the cantilever sensor. During exposure, there was no flow of air in or out of the chamber, allowing better quantification of the HCN concentration in the chamber. After exposure, the chamber was vented with a dry nitrogen flow. The exhaust from the chamber was routed into an HCN scrubber prior to external venting. Additional experiments were performed using fresh sensors that were exposed to $H_2SO_4$ vapors only, and sensors lacking the polymer or particle component (see Example 3).

Example 2

Exposure of the Sensor Material to Different Concentrations of HCN

Sensor material as described in Example 1 was also exposed to lower levels of HCN and the increase in polymer volume was detected using an EPM sensor. FIG. 2 shows the initial response of the sensor material to an exposure of approximately 150 ppm HCN. $H_2SO_4$ was added to KCN to evolve HCN at 139 second, as indicated by the arrow. As with the experiments described in Example 1, the initial sensor response was an increase in voltage, indicating that the microcantilever moved toward (into) the sensor material. The initial increase in sensor voltage was followed by a decrease in voltage, as before. The overall time frame for the response to the 150 ppm exposure was about 210 second, or approximately 5 times the length on the response time for 600 ppm HCN. The net voltage change from initial reading to final reading was approximately 0.15 mV, or ⅙ of the previous 600 ppm voltage response. The estimated net cantilever deflection from prior to exposure to end was 0.16 µm. It is expected that the net cantilever response for the 150 ppm exposure would be about ¼ of the response of the 600 ppm exposure instead of ⅙ (see discussion, above).

The response of the same sensor material to a second exposure of 150 ppm HCN was measured. This exposure occurred at 335 seconds, as indicated by the second/additional arrow shown in FIG. 3. The sensor was able to react a second time to the presence of HCN, indicating that the first 150 ppm exposure did not "exhaust" the sensing capability of the sensor material. The net sensor voltage response in the second exposure was approximately 0.1 mV, or about 35% less than that recorded in the first exposure. These results are reproducible using other samples of sensors material, and HCN detection signals vary 10-20% from one sensor to the next. This variation may be attributable to differences in the thickness of the sensing layer from one sensor to the next, since the sensors are assembled by hand, including deposition of the sensing layer.

Example 3

Negative Controls

Several negative control experiments were performed to confirm that the analyte sensor operated as predicted. The negative control experiments were performed in the absence of analyte, polymer matrix, or particles. The results of the experiments indicated that the analyte sensor requires both a polymer matrix components and solid particle component to respond to an analyte in the manner described. The polymer matrix or solid particle, alone without the other component, is ineffective as an analyte sensor, supporting the theory of operation.

1. No Analyte ($H_2SO_4$ Vapor Only)

Similar sensor material to that used in Examples 2 and 3 was exposed to $H_2SO_4$ vapors only, in the absence of a KCN analyte. Here, the sensor was present in the chamber when sulfuric acid was injected in through a rubber membrane with a syringe. The amount of acid vapor was similar to that present in the 600 ppm-experiment of Example 1. The results are shown in FIG. 3, with the arrow indicating the time at which the acid was injected. In comparing the sensor response to that shown in FIG. 2, it is apparent that $H_2SO_4$, by itself, had no significant effect on the sensor or sensing material.

2. No Polymer Matrix

A sensor was prepared that included a 20 µm gold wire without a polymer matrix. The sensor was exposed to 500 ppm HCN in a nitrogen atmosphere and the change in dimensions were measured using a cantilever device as before. The resistance of the cantilever device did not change in the presence of HCN, indicating that the gold wire did not respond to analyte in a manner similar to the polymer/particle sensor.

3. No Solid Material

A sensor was prepared that included a keratin polymer matrix without a solid particle. The sensor was exposed to 500 ppm HCN in a nitrogen atmosphere and the change in dimensions were measured using a cantilever device as before. The resistance of the cantilever device did not change in the presence of HCN, indicating that the keratin polymer matrix did not respond to analyte in a manner similar to the polymer/particle sensor.

Example 4

Sensor Material to Detect Carbon Monoxide

An exemplary sensing material was prepared for the detection of carbon monoxide. A polymercapto polymer, hereinafter referred to polymercaptoacrylate, was prepared in the following manner: To a 250 mL reaction flask were added 25 grams of butylmethacrylate, 10 g of ethyl hexylacrylate, 2 g of maleic anhydride, and 100 mL of ethyl acetate. Following homogenization, 0.1 g of azobisisobutyronitrile (AIBN) was added, and the mixture degassed with nitrogen gas for 25 minutes. The flask was then sealed and heated to 60° C. for 12 hours followed by 2 hours at 80° C. to yield a solution containing 28% solids anhydride containing acrylate polymer. To this solution were added dropwise 2 g of β-mercaptoethylamine and the reaction mixture was maintained at 60° C. for an additional hour.

Solvent was removed in vacuo to yield 32 g of a viscous, thiol-containing polymer. A nickel nanoparticle composite was prepared by combining 0.5 g of 80 nm nickel powder (Inframat Advanced Materials, LLC, Farmington, Conn., USA) and 0.1 g thiol polymer in 2 ml of ethyl acetate, and sonicacting for 30 minutes in an ultrasonic bath.

Sensors were prepared from polymercaptoacrylate and polybutylmethacrylate coethylhexylacrylate (a similar polymer lacking thiol moieties) as in Example 1, using a nanoparticle polymer matrix layer 20 µm thick. The polymer and particle components of the various sensors prepared are shown in Table 1.

TABLE 1

Polymer and particle components of various sensors

| Sensor | Nickel nanopowder (g) | Polymercapto-acrylate (g) | Polybutyl methacrylate co ethylhexylacrylate (g) |
|---|---|---|---|
| 1 | 0.5 | — | — |
| 2 | 0.5 | 1.0 | — |
| 3 | 0.5 | 0.1 | — |
| 4 | — | 1 | — |
| 5 | 0.5 | — | — |
| 6 | 0.5 | — | 0.5 |

Cantilevers were embedded in the sensor materials as above, and the sensors were placed in a controlled atmosphere chamber at 22° C. and monitored with a multichannel data acquisition system and 6-digit multimeter (Hewlett Packard). After equilibrating in a nitrogen atmosphere overnight, a stream of dry nitrogen gas was introduced and the resistivity of the sensors recorded. Preselected levels of carbon monoxide gas were then added to the feed gas and the resistance of then cantilever was measure and recorded after the sensor reaching steady state (typically 2 to 20 minutes depending on flow rate and concentration of carbon monoxide). Carbon monoxide was removed, the sensors reequilibrated, and a second dose of carbon monoxide introduced. The differences between the steady state and initial base line measurements are shown in Table 2.

TABLE 2

Measurements obtained using different sensors

| Sensor | 0 PPM CO | 100 PPM CO | 0 PPM CO | 50 PPM CO |
|---|---|---|---|---|
| 1 | 0 | <0.02 ohm | <.02 ohm | <.02 ohm |
| 2 | 0 | 0.4 ohm | <.02 ohm | 0.1 ohm |
| 3 | 0 | 2.8 ohm | <.02 ohm | 1.3 ohm |
| 4 | 0 | >.02 ohm | <.02 ohm | <0.02 ohm |
| 5 | 0 | <0.02 ohm | <.02 ohm | <0.02 ohm |
| 6 | 0 | <0.02 ohm | <.05 ohm | <0.02 ohm |

The results demonstrated that while neither nickel powder alone (Sensors 1 and 5) nor thiol polymer alone (Sensor 4) provided meaningful sensing data, the combination of the thiol-containing polymer with the nickel metal particles (Sensors 2 and 3) gave an excellent response, which was proportional to the level of CO present and returned to baseline in the absence of CO. A proposed reaction is a two step process. In the first step carbon monoxide displaces the thiol bonded to nickel which frees up a polymer chain, in a second step nickel and carbon monoxide may further react produce nickel carbonyl, $Ni(CO)_4$ as shown, below:

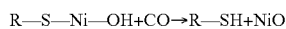

R—S—Ni—OH+CO→R—SH+NiO

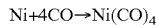

Ni+4CO→Ni(CO)$_4$

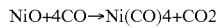

NiO+4CO→Ni(CO)4+CO2

A sensor made from the non-thiol containing polymer (polybutyl methacrylate co ethylhexyl acrylate), with or without nickel metal particles, was not effective in measuring the presence of CO, confirming the proposed mechanism of detection.

The optimum ratio of polymers to solid particles will vary depending on among other things, the surface area of the particles, the density of the polymer and particles and the type and amount of ligand functional groups but can readily be determined, e.g., using the above described procedures.

Example 4

Solvated Sensor Materials

An additional experiment was performed to determine if the results obtained with polymercaptoacrylate and nickel metal particles could be extended to sensor systems wherein the polymer was partially or fully solvated, for example, by an organic solvent, in the case of water insoluble polymers, or by water, in the case of water soluble or swellable polymers.

A polymer was prepared by polymerization of 97 parts of hydroxylpropyl acrylate (Dow Chemical) and 3 parts of carboxyethyl acrylate in water using potassium persulfate (0.15%) as an initiator. The resulting polymer was soluble in water. A sample of the polymer (5 g) was neutralized with ammonium hydroxide with stirring, and then combined with 8 g of 10 μm average-particle-size calcium carbonate. The resulting suspension was used to make a sensor as described, above. The ammonia was removed upon drying, resulting in a water insoluble but water swellable material. Without being limited to a theory, it is believed that the carboxylic acid groups of the polymer form associative bonds with the cationic surface of the calcium carbonate, providing the basis for a chemical sensor.

The sensor was placed in a solution of 50 mOsmol sodium chloride solution, and the response measures over the range of pH 3 to 7. The sensor response was essentially flat suggesting that interactions with the surface of the particles did not significantly change with the swelling of the polymer or the change in pH. This results in contrast with reports that carboxylic acid containing hydrogels are pH sensitive. However, this same sensor demonstrated a robust swelling response in the presence of 0.05 M benzoic acid. It is proposed that the benzoic acid was a more efficient ligand for the cationic particles, and that the benzoic acid displaced some of the carboxylic acid groups, changing the free volume of the sensor. This result suggests that the present sensor materials and methods apply to fully or partially solvated polymer materials, and that salvation is not primarily responsible for the signals produced from the present sensors.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A composition, comprising:
    a finely divided solid material dispersed in a substantially linear polymeric material having a free volume, the polymeric material and the solid material reversibly interacting in the presence and absence of an analyte to change the free volume of the polymeric material such that upon exposure to an analyte, the analyte competes with the polymeric material for interaction with the solid material, producing a detectable change in the free volume of the polymeric material, wherein the polymeric material is a polypeptide.

2. The composition of claim 1, wherein the polypeptide is a naturally-occurring fibrous protein.

3. The composition of claim 2, wherein the polypeptide is keratin.

4. The composition of claim 2, wherein the polypeptide is cysteine-rich polypeptide.

5. A composition, comprising:
    a finely divided solid material dispersed in a substantially linear polymeric material having a free volume, the polymeric material and the solid material reversibly interacting in the presence and absence of an analyte to change the free volume of the polymeric material such that upon exposure to an analyte, the analyte competes with the polymeric material for interaction with the solid material, producing a detectable change in the free volume of the polymeric material, wherein the polymeric material comprises polymercapto acrylate groups.

6. A method for detecting the presence of an analyte, comprising:
    providing a sensor material comprising a polymeric material and a finely divided solid material that interact via chemical bonds, the polymeric material having a free volume that is reduced upon interaction with the solid material and increased when the interaction with the solid material is reduced,
    exposing the sensor material to an analyte that competes with the polymeric material for interaction with the solid material, thereby reducing the interaction between the polymeric material and the solid matrix and increasing the free volume of the polymeric material, and detecting the increase in the free volume of the polymeric material,
wherein the increase in the free volume of the polymeric material corresponds to the presence of the analyte.

7. The method of claim 6, wherein the chemical bonds are covalent bonds.

8. The method of claim 7, wherein the covalent bonds are disulfide linkages.

9. The method of claim 6, wherein the polymeric material includes at least one chemical moiety selected from the group consisting of sulfides and amines.

10. The method of claim 6, wherein the polymeric material is a polypeptide.

11. The method of claim 6, wherein the polymeric material comprises polymercapto acrylate groups.

12. The method of claim 6, wherein the solid material is a metal.

13. The method of claim 6, wherein the analyte is a gas.

* * * * *